(12) United States Patent
Zhang et al.

(10) Patent No.: US 8,710,293 B2
(45) Date of Patent: Apr. 29, 2014

(54) ULTRATHIN FLUID-ABSORBENT CORES

(75) Inventors: Xiaomin Zhang, Charlotte, NC (US); Michael A. Mitchell, Waxhaw, NC (US)

(73) Assignee: BASF SE, Ludwigshafen (DE)

( * ) Notice: Subject to any disclaimer, the term of this patent is extended or adjusted under 35 U.S.C. 154(b) by 115 days.

(21) Appl. No.: 13/232,767

(22) Filed: Sep. 14, 2011

(65) Prior Publication Data
US 2012/0071848 A1 Mar. 22, 2012

Related U.S. Application Data

(60) Provisional application No. 61/384,719, filed on Sep. 21, 2010.

(51) Int. Cl.
*A61F 13/15* (2006.01)

(52) U.S. Cl.
USPC ............ 604/372; 604/368; 604/367; 604/374

(58) Field of Classification Search
USPC .................. 604/372, 368, 367, 374
See application file for complete search history.

(56) References Cited

U.S. PATENT DOCUMENTS

| | | | |
|---|---|---|---|
| 6,623,576 B2 | 9/2003 | Mitchell et al. | |
| 6,972,011 B2 | 12/2005 | Maeda et al. | |
| 7,662,460 B2 | 2/2010 | Herfert et al. | |
| 2003/0181115 A1 | 9/2003 | Nagasuna et al. | |
| 2005/0137085 A1 | 6/2005 | Zhang et al. | |
| 2006/0004336 A1 | 1/2006 | Zhang et al. | |
| 2007/0135785 A1 | 6/2007 | Qin et al. | |
| 2007/0156108 A1 | 7/2007 | Becker et al. | |
| 2008/0125735 A1 | 5/2008 | Busam et al. | |
| 2008/0312618 A1 | 12/2008 | Hundorf et al. | |

FOREIGN PATENT DOCUMENTS

| | | |
|---|---|---|
| EP | 1 293 187 A1 | 3/2003 |
| EP | 1 447 066 A1 | 8/2004 |
| EP | 1 447 067 A1 | 8/2004 |
| EP | 1 609 448 A1 | 12/2005 |
| JP | 2004/313580 A | 11/2004 |
| WO | WO-03/018671 A1 | 3/2003 |
| WO | WO-2004/071363 A1 | 8/2004 |
| WO | WO-2005/097025 A1 | 10/2005 |
| WO | WO-2008/155699 A1 | 12/2008 |
| WO | WO-2008/155701 A2 | 12/2008 |
| WO | WO-2008/155702 A1 | 12/2008 |
| WO | WO-2008/155710 A1 | 12/2008 |
| WO | WO-2008/155711 A1 | 12/2008 |
| WO | WO-2008/155722 A2 | 12/2008 |

OTHER PUBLICATIONS

Buchholz, Fredric L., et al.. *Modern Superabsorbent Polymer Technology*, "Commercial Processes for the Manufacture of Superabsorbent Polymers," New York: John Wiley & Sons, Inc., 1998, pp. 252-258.

Gould, Robert (editor), "Contact Angle, Wettability, and Adhesion," *Advances in Chemistry*, 1964, vol. 43, pp. 136-144 American Chemical Society (Washington, D.C.).

(Continued)

*Primary Examiner* — Jacqueline F. Stephens
(74) *Attorney, Agent, or Firm* — Marshall, Gerstein & Borun LLP

(57) ABSTRACT

The present invention relates to ultrathin fluid-absorbent cores comprising a substrate layer, multicomponent superabsorbent particles and an adhesive, wherein the wet SAP shake-out of superabsorbent particles out of the fluid-absorbent core is less than 10% by weight.

16 Claims, 1 Drawing Sheet

(56) References Cited

OTHER PUBLICATIONS

Chatterjee, P., et al. (editors), *Absorbency*, Elsevier, New York, 1985, pp. 60-68.

Morton, W., et al., Physical Properties of Textile Fibres, 2nd ed., the Textile Institute, (London: Heinemann, 1975).

International Search Report in international application No. PCT/EP2011/066319, Dec. 27, 2011.

ULTRATHIN FLUID-ABSORBENT CORES

CROSS-REFERENCE TO RELATED APPLICATIONS

This application claims the benefit of U.S. Provisional Patent Application No. 61/384,719, filed Sep. 21, 2010, incorporated herein by reference in its entirety.

DESCRIPTION

The present invention relates to ultrathin fluid-absorbent cores comprising a substrate layer, multicomponent superabsorbent particles and an adhesive, wherein the wet SAP shake-out (wetSAPloss) of superabsorbent particles out of the fluid-absorbent core is less than 10% by weight.

The production of fluid-absorbent articles is described in the monograph "Modern Superabsorbent Polymer Technology", F. L. Buchholz and A. T. Graham, Wiley-VCH, 1998, pages 252 to 258.

Fluid-absorbent articles such as disposable diapers typically comprise an upper liquid-pervious layer, a lower liquid-impervious layer, and a fluid-absorbent core between the upper and the lower layer. The fluid-absorbent cores typically comprise superabsorbent particles and fibers.

Ultrathin fluid absorbent cores can be formed by immobilization of superabsorbent particles on a nonwoven using hotmelt adhesives, i.e. forming longitudinal strips or discrete spots. Other patterns of the superabsorbent particles are also possible.

The preparation of ultrathin fluid-absorbent cores is described, for example, in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2.

The preparation of multicomponent superabsorbent particles (multicomponent SAP particles) is described, for example in U.S. Pat. Nos. 6,623,576, 7,662,460, and WO 03/018671 A1.

It was an object of the present invention to provide ultrathin fluid-absorbent cores having improved properties, i.e. a reduced dry SAP shake-out (drySAPloss) and a reduced wet SAP shake-out (wetSAPLoss) of superabsorbent particles.

The object is achieved by fluid-absorbent cores comprising a substrate layer, at least 75% by weight of multicomponent superabsorbent particles, comprising at least one crosslinked basic water-absorbing resin having a degree of neutralization of 0 to 50% and at least one crosslinked acidic water-absorbing resin having a degree of neutralization of 0 to 50%, less than 10% by weight of fibers and an adhesive, wherein the wet SAP shake-out of superabsorbent particles out of the fluid-absorbent core is less than 10% by weight.

It should be understood that fibers that are part of the substrate layers are not fibers in the sense of the present invention. The fluid-absorbent core comprise preferably less than 5% by weight, more preferably less than 2% by weight, most preferably less than 1% by weight, of fibers.

In a preferred embodiment of the present invention the fluid-absorbent cores are essential free of cellulose pulp fluff (fluffless fluid-absorbent cores).

The fluid-absorbent core comprises preferably at least 80% by weight, more preferably at least 83% by weight, most preferably at least 85% by weight, of the multicomponent superabsorbent particles.

The fluid-absorbent core comprises preferably not more than 15% by weight, more preferably not more than 10% by weight, most preferably not more than 7% by weight, of the adhesive.

In a preferred embodiment of the present invention a pressure sensitive adhesive is used that means that no solvent, water, or heat is needed to activate the adhesive. The substrate layer is preferably a nonwoven layer. Further, the fluid-absorbent cores can comprise two or more layers of multicomponent superabsorbent particles. The multicomponent superabsorbent particles are preferably placed in discrete regions of the fluid-absorbent core.

The dry SAP shake-out (drySAPLoss) of superabsorbent particles out of the fluid-absorbent core is preferably less than 5% by weight, more preferably less than 2% by weight, most preferably less than 1% by weight.

The wet SAP shake-out (wetSAPLoss) of superabsorbent particles out of the fluid-absorbent core is preferably less than 5% by weight, more preferably less than 2% by weight, most preferably less than 1% by weight.

The present invention further provides fluid-absorbent articles which comprise the inventive fluid-absorbent cores.

DETAILED DESCRIPTION OF THE INVENTION

A. Definitions

Figure 1:
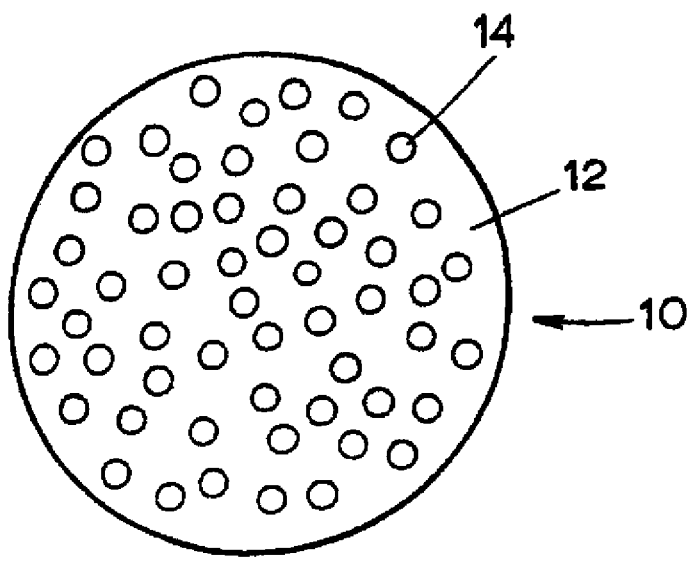
FIG. 1 is a schematic diagram of a multicomponent SAP particle having discrete microdomains of a dispersed resin in a continuous phase of a second resin.

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core" refers to a fluid-absorbent composition comprising superabsorbent particles. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein, the term "x-dimension" refers to the length, and the term "y-dimension" refers to the width of the fluid-absorbent composition, layer, core or article. Generally, the term "x-y dimension" refers to the plane, orthogonal to the height or thickness of the fluid-absorbent composition, layer, core or article.

As used herein, the term "z-dimension" refers to the dimension orthogonal to the length and width of the fluid-absorbent composition, layer, core or article. Generally, the term "z-dimension" refers to the height of the fluid-absorbent composition.

As used herein, the term "chassis" refers to fluid-absorbent material comprising the upper liquid-pervious layer and the lower liquid-impervious layer.

As used herein, the term "basis weight" indicates the weight of the fluid-absorbent core per square meter and it includes the chassis of the fluid-absorbent article. The basis weight is determined at discrete regions of the fluid-absorbent core: the front overall average is the basis weight of the fluid-absorbent core 5.5 cm forward of the center of the core to the front distal edge of the core; the insult zone is the basis weight of the fluid-absorbent core 5.5 cm forward and 0.5 cm backwards of the center of the core; the back overall average is the basis weight of the fluid-absorbent core 0.5 cm backward of the center of the core to the rear distal edge of the core.

As used herein, the term "density" indicates the weight of the fluid-absorbent core per volume and it includes the chassis of the fluid-absorbent article. The density is determined at discrete regions of the fluid-absorbent core: the front overall average is the density of the fluid-absorbent core 5.5 cm forward of the center of the core to the front distal edge of the core; the insult zone is the density of the fluid-absorbent core 5.5 cm forward and 0.5 cm backwards of the center of the core; the back overall average is the density of the fluid-absorbent core 0.5 cm backward of the center of the core to the rear distal edge of the core.

Further, it should be understood, that the term "upper" refers to fluid-absorbent compositions which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the composition which is furthermost away from the wearer of the fluid-absorbent article, hereinafter described as "lower liquid-impervious layer".

As used herein, the term "liquid-pervious" refers to a substrate, layer or laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

Fluid-absorbent articles comprising more than one fluid-absorbent core, in a preferred manner comprising a double-core system including an upper core and a lower core, hereinafter called "primary core" and "secondary core".

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "section" or "zone" refers to a definite region of the fluid-absorbent composition.

As used herein, the term "article" refers to any three-dimensional solid material being able to acquire and store fluids discharged from the body. Preferred articles according to the present invention are disposable fluid-absorbent articles that are designed to be worn in contact with the body of a user such as disposable fluid-absorbent pantiliners, sanitary napkins, catamenials, incontinence inserts/pads, diapers, training pant diapers, breast pads, interlabial inserts/pads and the like.

As used herein, the term "body fluids" refers to any fluid produced and discharged by human or animal body, such as urine, menstrual fluids, faeces, vaginal secretions and the like.

B. Multicomponent Superabsorbent Particles

Each multicomponent SAP particle of the present invention contains at least one acidic water-absorbing resin and at least one basic water-absorbing resin. In one embodiment, the SAP particles consist essentially of acidic resins and basic resins, and contain microdomains of the acidic and/or basic resins. In another embodiment, microdomains of the acidic and basic resins are dispersed throughout an absorbent matrix resin.

The multicomponent SAP particles are analogous to liquid emulsions wherein small droplets of a first liquid, i.e., the dispersed phase, are dispersed in a second liquid, i.e., the continuous phase. The first and second liquids are immiscible, and the first liquid, therefore, is homogeneously dispersed in the second liquid. The first liquid can be water or oil based, and conversely, the second liquid is oil or water based, respectively.

Therefore, in one embodiment, the multicomponent SAP particles of the present invention can be envisioned as microdomains of an acidic resin dispersed in a continuous phase of a basic resin, or as microdomains of a basic resin dispersed in a continuous acid resin. These multicomponent SAP particles are illustrated in FIG. 1 showing a multicomponent SAP particle 10 having discrete microdomains 14 of a dispersed resin in a continuous phase of a second resin 12. If microdomains 14 comprise an acidic resin, then continuous phase 12 comprises a basic resin. Conversely, if microdomains 14 comprise a basic resin, then continuous phase 12 is an acidic resin.

Figure 2:
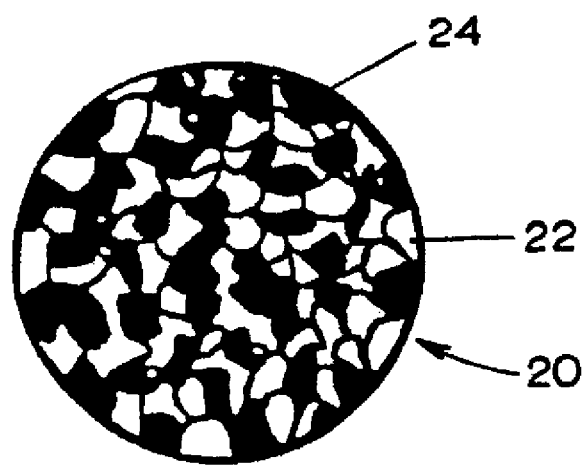
FIG. 2 is a schematic diagram of a multicomponent SAP particle having a plurality of microdomains of an acidic resin and a plurality of microdomains of a basic resin dispersed throughout the particle.

In another embodiment, the SAP particles are envisioned as microdomains of an acidic resin and microdomains of a basic resin dispersed throughout each particle, without a continuous phase. This embodiment is illustrated in FIG. 2, showing a multicomponent SAP particle 20 having a plurality of microdomains of an acidic resin 22 and a plurality of microdomains of a basic resin 24 dispersed throughout the particle.

In yet another embodiment, microdomains of the acidic and basic resins are dispersed throughout a continuous phase comprising a matrix resin. This embodiment also is illustrated in FIG. 1 wherein a multicomponent SAP particle 10 contains microdomains 14 of acidic resin and basic resin dispersed in a continuous phase 12 of a matrix resin.

The multicomponent SAP particles therefore comprise an acidic resin and a basic resin in a weight ratio of preferably 5:95 to 95:5, more preferably 10:90 to 90:10 and most preferably 20:80 to 80:20. To achieve the full advantage of the present invention, the weight ratio of acidic resin to basic resin in a multicomponent SAP particle is 30:70 to 70:30.

The multicomponent SAP particles contain preferably at least 50%, and more preferably at least 70%, by weight of acidic resin plus basic resin. To achieve the full advantage of the present invention, a multicomponent SAP particle contains 80% to 100% by weight of the acidic resin plus basic resin. Components of the present SAP particles, other than the acidic and basic resin, typically, are matrix resins or other minor optional ingredients.

The multicomponent SAP particles can be in any form, such as granules, beads, powders, flakes, or any other desired shape. In embodiments wherein the multicomponent SAP is prepared using an extrusion step, the shape of the SAP is determined by the shape of the extrusion dye.

Preferably, the present SAP particles are in the form of a granule or a bead, having a particle size of preferably 10 to 10,000 μm, and more preferably 100 to 1,000 mm. To achieve the full advantage of the present invention, the multicomponent SAP particles have a particle size of 150 to 800 μm Each multicomponent SAP particle contains a plurality of microdomains of an acidic water-absorbing resin and/or a basic water-absorbing resin. As illustrated hereafter, the microdomain structure of the present SAP particles provides improved water absorption and retention compared to an SAP comprising a simple mixture of discrete acidic SAP resin particles and basic SAP resin particles. The improved absorption and retention, especially of electrolyte-containing liquids, by the present multicomponent SAP particles, is attributed, in part, to the fact that electrolyte removal from the liquid is facilitated by contacting a single particle (which, in effect, performs an essentially simultaneous deionization of the liquid), as opposed to the liquid having to contact individual acidic and basic particles (which, in effect, performs a sequential two-step deionization).

The present multicomponent SAP particles, therefore, can be in a form wherein microdomains of an acidic water-absorbing resin are dispersed throughout a continuous phase of a basic water-absorbing resin. Alternatively, the multicomponent SAP can be in a form wherein microdomains of a basic resin are dispersed throughout a continuous phase of an acidic resin. In another embodiment, microdomains of one or more acidic resin and microdomains of one or more basic resin comprise the entire SAP particle, and neither type of resin is considered the dispersed or the continuous phase. In yet another embodiment, microdomains of an acidic resin and microdomains of a basic resin are homogeneously dispersed throughout a matrix resin.

An acidic water-absorbing resin present in a multicomponent SAP particle can be either a strong or a weak acidic water-absorbing resin. The identity of the acidic water-absorbing resin is not limited as long as the resin is capable of swelling and absorbing at least ten times its weight in water, when in a neutralized form. The acidic resin is present in its acidic form, i.e., 75% to 100% of the acidic moieties are present in the free acid form. As illustrated hereafter, although the free acid form of a acidic water-absorbing resin is generally a poor water absorbent, the combination of an acidic resin and a basic resin in a present multicomponent SAP particle provides excellent water absorption and retention properties.

The acidic water-absorbing resin typically is a lightly crosslinked acrylic-type resin, like lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity of the polymer.

As set forth above, polymerization of acidic monomers most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than 20%, preferably less than 10%, and most preferably 0.01% to 7%.

A crosslinking agent most preferably is used in an amount of less than 7 wt %, and typically 0.1 wt % to 5 wt %, based on the total weight of monomers. Examples of crosslinking polyvinyl monomers include, but are not limited to, polyacrylic (or polymethacrylic) acid esters and bisacrylamides.

The polyacrylic (or polymethacrylic) acid esters are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The bisacrylami-des are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacylate, trimethylolpropane triacrylate, trimethylolpropane trimethacrylate, tris(2-hydroxy-ethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, or mixtures thereof. Compounds like divinylbenzene and divinyl ether also can be used to crosslink the poly(dialkyl-aminoalkyl acrylamides). Especially preferred crosslinking agents are N,N'-methylenebisacry-lamide, N,N'-methylenebismethacrylamide, ethylene glycol dimethacrylate, and trimethylolpropane triacrylate.

The acidic resin, either strongly acidic or weakly acidic, can be any resin that acts as an superabsorbent in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly (vinylsulfonic acid), poly(vinyl-phosphonic acid), poly(vinylphosphoric acid), poly(vinylsulfuric acid), sulfonated polystyrene, and mixtures thereof. The preferred acidic resins are the polyacrylic acids.

The multicomponent SAP particles can contain individual microdomains that (a) contain a single acidic resin or (b) contain more than one, i.e., a mixture, of acidic resins. The multicomponent SAP particles also can contain microdomains wherein a portion of the microdomains contain a first acidic resin or acidic resin mixture, and the remaining portion contains a second acid resin or acidic resin mixture.

Analogous to the acidic resin, the basic water-absorbing resin present in the present multicomponent SAP particles can be a strong or weak basic water-absorbing resin. The identity of the basic resin is not limited as long as the basic resin is capable of swelling and absorbing at least 10 times its weight in water, when in a charged form. The weak basic resin typically is present in its free base, or neutral, form, i.e., 75% to 100% of the basic moieties, e.g., amino groups, are present in a neutral, uncharged form. The strong basic resins typically are present in the hydroxide (OH) form.

The basic water-absorbing resin typically is a lightly crosslinked acrylic type resin, like a poly(vinylamine) or a poly(dialkylaminoalkyl(meth)acrylamide). The basic resin also can be a polymer such as a lightly crosslinked polyethylenimine, a poly(vinylguanidine), a poly(dimethyldiallylammonium hydroxide), a quaternized polystyrene derivative, a guanidine-modified polystyrene, or a quaternized poly((meth)acrylamide) or ester analog.

The lightly crosslinked basic water-absorbing resin can contain other polymerizable units and is crosslinked using a polyfunctional organic compound, as set forth above with respect to the acidic water-absorbing resin.

A basic water-absorbing resin used in the present multicomponet SAP particles typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., ZA(O2)O—(CH2)n-OS(O)2Z, wherein n is 1 to 10, and Z is methyl or tosyl), multifunctional epoxides (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from E.I. du Pont de Nemours, Wilmington, Del., U.S.A.), melamine resins (e.g., CYMEL 301, CYMEL 303, CYMEL 370, and CYMEL 373 from Cytec Industries, Wayne, N.J., U.S.A.), hydroxymethyl ureas (e.g., N,N'-dihydroxyroethyl-4,5-dihydroxy-ethyleneurea), and multifunctional isocyanates (e.g., toluene diisocyanate). Crosslinking agents also are disclosed in U.S. Pat. No. 5,085,787 and in EP 0 450 923 A1.

In general, the crosslinking agent should be water or alcohol soluble and possess sufficient reactivity with the basic resin such that crosslinking occurs in a controlled fashion, preferably at a temperature of 25 to 150° C. Preferred crosslinking agents are ethylene glycol diglycidyl ether (EGDGE), a water-soluble diglycidyl ether, and a dibromoalkane, an alcohol-soluble compound.

The basic resin, either strongly or weakly basic, therefore, can be any resin that acts as an superabsorbent in its charged form. The basic resin typically contains amino or guanidino moieties. Examples of basic resins include a poly(vinylamine), a polyethylenimine, a poly(vinylguani-dine), or a poly(dialkylaminoalkyl(meth)acrylamide). The preferred basic resins are the poly(vi-nylamine)s. Analogous to microdomains containing an acidic resin, the present multicomponent SAP particles can contain microdomains of a single basic resin, microdomains containing a mixture of basic resins, or microdomains of different basic resins.

The present multicomponent SAP particles can be prepared by various methods. It should be understood that the exact method of preparing a multicomponent SAP is not limited by the following embodiments. Any method that provides a particle having microdomains of an acidic and/or basic resin in intimate contact with each other or a continuous phase of an acidic resin, basic resin, and/or matrix resin is suitable.

In one method, dry particles of a basic resin, optionally surface crosslinked, are admixed into a rubbery gel of an acidic resin. The resulting mixture is extruded, then dried, and optionally surface crosslinked, to provide multicomponent SAP particles having microdomains of a basic resin homogeneously dispersed throughout a continuous phase of an acidic resin. Alternatively, particles of an acidic resin, optionally surface crosslinked, can be admixed into a rubbery gel of a basic resin, and the resulting mixture is extruded and dried, and optionally surface crosslinked, to provide multicomponent SAP particles having microdomains of an acidic resin homogeneously dispersed throughout a continuous phase of a basic resin. The method also can be employed using dry particles of an acidic resin and a gel of a basic resin.

In another method, dry particles of an acidic resin can be admixed with dry particles of a basic resin, and the resulting mixture is formed into a hydrogel, then extruded, to form multicomponent SAP particles.

In yet another method, a rubbery gel of an acidic resin and a rubbery gel of a basic resin, each optionally surface crosslinked, are coextruded, and the coextruded product is dried, and optionally surface crosslinked, to form multicomponent SAP particles containing microdomains of the acidic resin and the basic resin dispersed throughout the particle.

The method of preparing the present multicomponent SAP particles, therefore, is not limited, and does not require an extrusion step. Persons skilled in the art are aware of other methods wherein the multicomponent SAP contains microdomains of an acidic resin and/or a basic resin cure in intimate contact with each other, with a matrix resin, or with an acidic and/or basic resin. One example is agglomeration of an acidic and/or basic resin with each other or another acidic and/or basic resin to provide a multicomponent SAP particle containing microdomains of an acidic and/or a basic resin.

In embodiments wherein an acidic resin and a basic resin are present as microdomains within a matrix of a matrix resin, particles of an acidic resin and a basic resin are admixed with a rubbery gel of a matrix resin, and the resulting mixture is extruded, then dried, to form multicomponent SAP particles having microdomains of an acidic resin and a basic resin dispersed in a continuous phase of a matrix resin. Alternatively, rubbery gels of an acidic resin, basic resin, and matrix resin can be coextruded to provide a multicomponent SAP containing microdomains of an acidic resin, a basic resin, and a matrix resin dispersed throughout the particle. In this embodiment, the acidic resin, basic resin, and resulting multicomponent SAP particles, each can be optionally surface crosslinked.

The matrix resin is any resin that allows fluid transport such that a liquid medium can contact the acidic and/or basic resin. The matrix resin typically is a hydrophilic resin capable of absorbing water. Nonlimiting examples of matrix resins include poly(vinyl alcohol), poly(N-vinylform-amide), polyethylene oxide, poly(meth)acrylamide, poly(hydroxyethyl acrylate), hydroxyethylcellulose, methylcellulose, and mixtures thereof. The matrix resin also can be a conventional water-absorbing resin, for example, a polyacrylic acid neutralized greater than 25 mole %, and typically greater than 50 mole %.

In preferred embodiments, the acidic resin, the basic resin, and/or the multicomponent SAP particles are surface crosslinked. In especially preferred embodiments, the acidic and/or basic resins comprising the multicomponent SAP particles are surface crosslinked, and the entire multicomponent SAP particle is surface crosslinked. It has been found that surface crosslinking of an acidic resin, a basic resin, and/or a multicoroponent SAP particle enhances the ability of the resin or multicomponent SAP particle to absorb and retain aqueous media under a load.

Surface crosslinking is achieved by spraying an acidic resin, a basic resin, and/or a multicomponent SAP particle with a solution of a surface crosslinking agent to wet predominantly only the outer surfaces of the resin or SAP particle. Surface crosslinking and drying of the resin or SAP particle then is performed, preferably by heating at least the wetted surfaces of the resin or SAP particles.

Typically, the resins and/or SAP particles are surface treated with an aqueous or an alcoholic solution of a surface crosslinking agent. The solution contains preferably 0.01% to 4%, and more preferably 0.4% to 2%, by weight, surface crosslinking agent in a suitable solvent. The solution can be applied as a fine spray onto the surface of freely tumbling resin particles or multicomponent SAP particles at a ratio of preferably 1:0.01 to 1:0.5 parts by weight resin or SAP particles to solution of surface crosslinking agent. The surface crosslinker is present in amount of preferably 0% to 1%, and more preferably 0% to 0.5%, by weight of the resin or SAP particle. To achieve the full advantage of the present invention, the surface crosslinker is present in an amount of 0.001% to 0.1% by weight of the resin or SAP particle.

The crosslinking reaction and drying of the surface-treated resin or multicomponent SAP particles are achieved by heating the surface-treated polymer at a suitable temperature, e.g., 25 to 150° C., and preferably 105 to 120° C. However, any other method of reacting the crosslinking agent to achieve surface crosslinking of the resin or multicomponent SAP particles, and any other method of drying the resin or multicomponent SAP particles, such as microwave energy, or the like, can be used.

With respect to the basic resin, or multicomponent SAP particles having a basic resin present on the exterior surface of the particles, suitable surface crosslinking agents include di- or polyfunctional molecules capable of reacting with amino groups and crosslinking a basic resin. Preferably, the surface crosslinking agent is alcohol or water soluble and possesses sufficient reactivity with a basic resin such that crosslinking occurs in a controlled fashion at a temperature of 25 to 150° C.

Nonlimiting examples of suitable surface crosslinking agents for basic resins include:
 a) dihalides and disulfonate esters,
 b) multifunctional aziridines,
 c) multifunctional aldehydes, for example, glutaraldehyde, trioxane, paraformaldehyde, terephthaldehyde, malonaldehyde, and glyoxal, and acetals and bisulfites thereof,
 d) halohydrins, like epichlorohydrin,
 e) multifunctional epoxy compounds, for example, ethylene glycol diglycidyl ether, bisphenol A diglycidyl ether, and bisphenol F diglycidyl ether,
 f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, like oxalic acid, adipic acid, succinic acid, dodecanoic acid, malonic acid, and glutaric acid, and esters, anhydrides, and acid chlorides derived therefrom,
 g) organic titanates, like TYZOR AA, available from E.I. du Pont de Nemours, Wilmington, Del., U.S.A.,
 h) melamine resins, like the CYMEL resins available from Cytec Industries, Wayne, N.J., U.S.A.,
 i) hydroxymethyl ureas, like N,N'-dihydroxymethyl-4,5-dihydroxyethylene urea,
 j) multifunctional isocyanates, like toluene diisocyanate, isophorone diisocyanate, xylene diisocyanate, and hexamethylene diisocyanate, and
 k) other crosslinking agents for basic water-absorbing resins known to persons skilled in the art.

A preferred surface crosslinking agent is a dihaloalkane, ethylene glycol diglycidyl ether (EGDGE), or a mixture thereof, which crosslink a basic resin at a temperature of preferably 25 to 150° C. Especially preferred surface crosslinking agents are dibromoalkanes containing 3 to 10 carbon atoms and EGDGE.

With respect to the acidic water-absorbing resins, or multicomponent SAP particles having an acidic resin on the exterior surface of the particles, suitable surface crosslinking agents are capable of reacting with acid moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of 25 to 150° C.

Nonlimiting examples of suitable surface crosslinking agents for acidic resins include:
 a) polyhydroxy compounds, like glycols and glycerol,
 b) metal salts,
 c) quaternary ammonium compounds,
 d) a multifunctional epoxy compound,
 e) an alkylene carbonate, like ethylene carbonate or propylene carbonate,
 f) a polyaziridine, like 2,2-bishydroxymethyl butanol tris [3-(1-aziridine propionate]),
 g) a haloepoxy, like epichlorhydrin,
 h) a polyamine, like ethylenediamine,
 i) a polyisocyanate, like 2,4-toluene diisocyanate, and
 j) other crosslinking agents for acidic water-absorbing resins known to persons skilled in the art.

Either the acidic resin or the basic resin can be the continuous phase of a present multicomponent SAP particle Likewise, either the acidic resin or the basic resin can be the dispersed microdomain phase. In addition, a strong acidic resin can be used with either a strong basic resin or a weak basic resin. A weak acidic resin can be used with a strong basic resin or a weak basic resin. Preferably, the acidic resin is a weak acidic resin and the basic resin is a weak basic resin. In preferred embodiments, the weak acidic resin, the weak basic resin, and/or the multicomponent SAP particles are surface crosslinked.

As previously discussed, sodium poly(acrylate) is considered the best superabsorbent, and, therefore, is the most widely used superabsorbent in commercial applications. Sodium poly(acrylate) has polyelectrolytic properties that are responsible for its superior performance in absorbent applications. These properties include a high charge density, and charge relatively close to the polymer backbone.

However, an acidic resin in the free acid form, or a basic resin in the free base form, typically do not function as a superabsorbent because there is no ionic charge on either type of polymer. A poly(acrylic acid) resin, or a poly(vinylamine) resin, are neutral polymers, and, accordingly, do not possess the polyelectrolytic properties necessary to provide a superabsorbent. The driving force for water absorption and retention, therefore, is lacking. However, when converted to a salt, an acidic resin, like a polyacrylic acidic or a basic resin, like a poly(dialkylaminoalkyl(meth)acrylamide), then behave like a superabsorbent.

It has been found that basic resins, in their free base form, are useful components in superabsorbent materials further containing an acidic water-absorbing resin. For example, a superabsorbent material comprising an admixture of a poly (dialkyl-aminoalkyl(meth)acrylamide) and an acidic water-absorbing resin, like polyacrylic acid, demonstrates good water absorption and retention properties. Such a superabsorbent material comprises two uncharged, slightly crosslinked polymers, each of which is capable of swelling and absorbing aqueous media. When contacted with water or an aqueous electrolyte-containing medium, the two uncharged polymers neutralize each other to form a superabsorbent material. This also reduces the electrolyte content of the medium absorbed by polymer, further enhancing the polyelectrolyte effect. Neither polymer in its uncharged form behaves as a superabsorbent by itself when contacted with water. However, superabsorbent materials, which contain a simple mixture of two resins, one acidic and one basic, are capable of acting as an absorbent material because the two resins are converted to their polyelectrolyte form. These superabsorbent materials have demonstrated good water absorption and retention properties. However, the present multicomponent SAP particles, containing microdomains of an acidic resin and/or a basic resin, exhibit improved water absorption and retention over simple mixtures of acidic resin particles and basic resin particles.

In the present multicomponent SAP particles, the weak basic resin is present in its free base, e.g., amine, form, and the acidic resin is present in its free acid form. It is envisioned that a low percentage, i.e., 25% or less, of the amine and/or acid functionalities can be in their charged form. The low percentage of charged functionalities does not adversely affect performance of the multicomponent SAP particles, and can assist in the initial absorption of a liquid. A strong basic resin is present in the hydroxide, or charged, form.

The multicomponent SAP particles are an essential element of the inventive fluid-absorbent cores of the present invention. The multicomponent SAP particles can be used to prepare fluid-absorbent cores having an improved dry SAP shake-out (drySAPloss). Combining the multicomponent SAP particles, an adhesive, and a substrate layer to fluffless fluid-absorbent cores reduces also the wet SAP shake-out (wetSAPloss).

C. Fluid-Absorbent Articles

The fluid-absorbent article comprises of (A) an upper liquid-pervious layer (B) a lower liquid-impervious layer (C) a fluid-absorbent core between (A) and (B) comprising an optional core cover, a fluid-storage layer comprising at least 75% by weight multicomponent superabsorbent particles and an adhesive;

preferably at least 80% by weight multicomponent superabsorbent particles and an adhesive;

more preferably at least 83% by weight multicomponent superabsorbent particles and an adhesive;

most preferably at least 85% by weight multicomponent superabsorbent particles and an adhesive;

(D) an optional acquisition-distribution layer between (A) and (C), comprising at least 80% by weight fibrous material and superabsorbent particles;

preferably at least 85% by weight fibrous material and superabsorbent particles;

more preferably at least 90% by weight fibrous material and superabsorbent particles;

most preferably at least 95% by weight fibrous material and superabsorbent particles;

(E) an optional tissue layer disposed immediately above and/or below (C); and (F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally superabsorbent particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapor breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

Liquid-Pervious Layer (A)

The liquid-pervious layer (A) is the layer which is in direct contact with the skin. Thus, the liquid-pervious layer is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious layer is the acquisition and transport of body fluids from the wearer towards the fluid-absorbent core. Typically liquid-pervious layers are formed from any materials known in the art such as nonwoven material, films or combinations thereof. Suitable liquid-pervious layers (A) consist of customary synthetic or semisynthetic fibers or bicomponent fibers or films of polyester, polyolefins, rayon or natural fibers or any combinations thereof. In the case of nonwoven materials, the fibers should generally be bound by binders such as polyacrylates. Additionally the liquid-pervious layer may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydroformed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

Suitable wood pulp fibers can be obtained by chemical processes such as the Kraft and sulfite processes, as well as from mechanical processes, such as ground wood, refiner mechanical, thermo-mechanical, chemi-mechanical and chemi-thermo-mechanical pulp processes. Further, recycled wood pulp fibers, bleached, unbleached, elementally chlorine free (ECF) or total chlorine free (TCF) wood pulp fibers can be used.

The fibrous material may comprise only natural fibers or synthetic fibers or any combination thereof. Preferred materials are polyester, rayon and blends thereof, polyethylene, and polypropylene.

The fibrous material as a component of the fluid-absorbent compositions may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of superabsorbent particles of the resulting fluid-absorbent composition. Such, the use of hydrophobic fibers is preferred if the fluid-absorbent composition is adjacent to the wearer of the fluid-absorbent article, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e.g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of rising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between 75 C and 175 C. The typical length of thermoplastic fibers is from 0.4 to 6 cm, preferably from 0.5 to 1 cm. The diameter of thermoplastic fibers is defined in terms of either denier (grams per 9000 meters) or dtex (grams per 10 000 meters). Typical thermoplastic fibers have a dtex in the range from 1.2 to 20, preferably from 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermal treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers. For example, the thickness of the layer is very important and influences together with its x-y dimension the acquisition-distribution behavior of the layer. If there is further some profiled structure integrated, the acquisition-distribution behavior can be directed depending on the three-dimensional structure of the layer. Thus 3D-polyethylene in the function of liquid-pervious layer is preferred.

Thus, suitable liquid-pervious layers (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious layers (A) extend partially or wholly across the fluid-absorbent structure and can extend into and/or form part of all the preferred sideflaps, side wrapping elements, wings and ears.

Liquid-Impervious Layer (B)

The liquid-impervious layer (B) prevents the exudates absorbed and retained by the fluid-absorbent core from wetting articles which are in contact with the fluid-absorbent article, as for example bedsheets, pants, pajamas and undergarments. The liquid-impervious layer (B) may thus comprise a woven or a nonwoven material, polymeric films such as thermoplastic film of polyethylene or polypropylene, or composite materials such as film-coated nonwoven material.

Suitable liquid-impervious layers include nonwoven, plastics and/or laminates of plastic and nonwoven. Both, the plastics and/or laminates of plastic and nonwoven may appropriately be breathable, that is, the liquid-impervious layer (B) can permit vapors to escape from the fluid-absorbent material. Thus the liquid-impervious layer has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious layers are permeable for vapor. Preferably the liquid-impervious layer is constructed from vapor permeable material showing a water vapor transmission rate (WVTR) of at least 100 gsm per 24 hours, preferably at least 250 gsm per 24 hours and most preferred at least 500 gsm per 24 hours.

Preferably the liquid-impervious layer (B) is made of nonwoven comprising hydrophobic materials, e.g. synthetic fibers or a liquid-impervious polymeric film comprising plastics e.g. polyethylene. The thickness of the liquid-impervious layer is preferably 15 to 30 µm.

Further, the liquid-impervious layer (B) is preferably made of a laminate of nonwoven and plastics comprising a nonwoven having a density of 12 to 15 gsm and a polyethylene layer having a thickness of 10 to 20 µm.

The typically liquid-impervious layer (B) extends partially or wholly across the fluid-absorbent structure and can extend into and/or form part of all the preferred sideflaps, side wrapping elements, wings and ears.

Fluid-Absorbent Core (C)

The fluid-absorbent core (C) is disposed between the upper liquid-pervious layer (A) and the lower liquid-impervious layer (B). Suitable fluid-absorbent cores (C) may be selected from any of the fluid-absorbent core-systems known in the art provided that requirements such as vapor permeability, flexibility and thickness are met. Suitable fluid-absorbent cores refer to any fluid-absorbent composition whose primary function is to acquire, transport, distribute, absorb, store and retain discharged body fluids.

The top view area of the fluid-absorbent core (C) is preferably at least 200 cm$^2$, more preferably at least 250 cm$^2$, most preferably at least 300 cm$^2$. The top view area is the part of the core that is face-to-face to the upper liquid-pervious layer.

The inventive fluid-absorbent core comprises a substrate layer, i.e. a nonwoven layer or a tissue paper, multicomponent superabsorbent particles, and an adhesive.

Suitable nonwoven layers for the present invention include those made using synthetic polymeric fibers. The synthetic polymeric fibers may be formed from any polymeric material capable of forming fibers which fibers can be formed into a nonwoven layer. Suitable polymeric material from which the synthetic polymeric fibers may be formed include polyolefins, such as polyethylene, polypropylene, and the like, polyesters such as polyethylene terephthalate and the like, polyamides such as nylon 6, nylon 6,6, poly (iminocarboxylpentamethylene) and the like, acrylics, and modified cellulosic material, such as cellulose acetate and rayon; as well as mixtures and copolymers thereof.

The synthetic polymeric fibers may be formed by meltblowing, through a spunbond process, by extrusion and drawing, or other wet, dry and melt spinning methods known to those skilled in the art. The synthetic polymeric fibers from which the nonwoven layer is formed may have a discrete length or may be substantially continuous. For example, if the synthetic polymeric fibers are formed by meltblowing, the fibers may be substantially continuous (few visible ends). If the fibers are formed by extrusion and drawing to produce a tow, the tow may be used as produced or cut into staple fibers having a length, for example, of from 25 to 75 mm or short cut into lengths of from 1 to 25 mm. The synthetic polymeric fibers may suitably have a maximum cross-sectional dimension of from 0.5 to 50 µm as determined by microscopic measurement using an optical microscope and a calibrated stage micrometer or by measurement from Scanning Electron photomicrographs.

The nonwoven layers may be formed directly through a spunbond or meltblown process, or by carding or air-laying staple or short cut fibers. Other methods of forming nonwoven layers known to those skilled in the art may be suited for use in the present invention. The nonwoven layer may subsequently be bonded to enhance structural integrity. Methods of bonding nonwoven layers are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known to those skilled in the art as bicomponent fibers.

The nonwoven layer may be formed from a single type of synthetic polymeric fiber or may contain synthetic polymeric fibers formed from different polymeric materials, having different fiber lengths or maximum cross-sectional dimensions. For example, the nonwoven layer may comprise a mixture of (1) bicomponent fibers having a polyethylene sheath and a polypropylene core which bicomponent fibers have a maximum cross-sectional dimension of 20 µm and a length of 38 mm and (2) polyester fibers, i.e. polyethylene terephthalate, having a maximum cross-sectional dimension of 25 µm and a length of 38 mm. Fibers 1 and 2 may be combined in a weight ratio of from 1:99 to 99:1. The fibers may be uniformly mixed or may be concentrated at opposite planar surfaces of the nonwoven layer.

The nonwoven layer suitably comprises preferably from 20 to 100% by weight, more preferably from 25 to 100% by weight, most preferably from 50 to 100% by weight, synthetic polymeric fibers. In addition to the synthetic polymeric fibers, the nonwoven layer may contain from 90 to 0% by weight of a non-synthetic polymeric fiber such as wood pulp fluff cotton linters, cotton, and the like.

In one preferred embodiment, the nonwoven layer contains synthetic polymeric fibers which are formed from a polymeric material having a high wet modulus. The importance of the modulus of a material is discussed in the monograph "Absorbency", P. K. Chatterjee, Elsevier, 1985. A polymeric material will be considered to have a high wet modulus when it has a wet modulus greater than 80% of its dry modulus as determined by the ASTM test method D 2101-91 using modified gauge lengths. It is often desired to form the synthetic polymeric fibers of the nonwoven layer from a polymeric material having a high wet modulus because such materials generally form nonwoven layers which possess a relatively high degree of wet resiliency. The wet resilience of a nonwoven layer is related to the pore structure (while under a load) of the nonwoven layer. As will be discussed in greater detail below, it is often desired that the nonwoven layer have a relatively high degree of wet resilience.

The pore structure (while under a load) of a fibrous structure formed from fibers of a polymeric material will, as discussed above, relate to the wet and/or dry modulus of the constituent fibers. Wet modulus of the constituent fibers should be considered for fibers that may likely be wetted during use. For the purposes of estimating the effect of load on the pore structure of a fibrous structure formed from fibers of a polymeric material the tensile modulus of the fiber which can be related to the flexural rigidity of the fiber as shown in the monograph "Physical Properties of Textile Fibers", W. E. Morton and J. W. S. Hearl, The Textile Institute, 1975, can be used.

As a general rule, the polymeric materials from which the synthetic polymeric fibers of the nonwoven layer are formed will be inherently hydrophobic. As used herein, a polymeric material will be considered to be "inherently" hydrophobic or hydrophilic when the polymeric material, free from any surface modifications or treatments, e.g., surface active agents, spin finishes, blooming agents, etc., is hydrophobic or hydrophilic, respectively.

When the synthetic polymeric fibers of the nonwoven layer are formed from a polymeric material which is inherently hydrophobic, it is often desirable to treat the fibers with a surface modifying material to render the surface of the fiber hydrophilic. For example, a surfactant may be applied to the fibers.

The nonwoven layer may also comprise hydrophilic fibers. The hydrophilic materials may be inherently hydrophilic such as cellulosic fibers such as wood pulp fluff, cotton linters, and the like, regenerated cellulose fibers such as rayon, or certain nylon copolymers such as poly(pentamethylenecarbonamide) (nylon-6)/polyethylene oxide. Alternatively, the hydrophilic fibers may be hydrophobic fibers which have been treated to possess a hydrophilic surface. For example, the fibers may be formed from a polyolefin material which is subsequently coated with a surface active agent such that the fiber itself is hydrophilic as described herein. Other methods of hydro-philizing fibers formed from hydrophobic materials are known and suited for use in the present invention.

Methods of providing inherently hydrophilic fibers such as wood pulp fluff are known. Hydrophobic fibers which can be treated to possess a hydrophilic surface are suitably formed by processes known to those skilled in the art. If the hydrophilic fibers are hydrophobic fibers which have been treated to possess a hydrophilic surface, the fibers will suitably have a fiber length and maximum cross-sectional dimension as set forth above. If the hydrophilic fibers are inherently hydrophilic such as wood pulp fluff, rayon, cotton, cotton linters and the like, the fibers will generally have a length of from 1.0 to 50 mm and a maximum cross-sectional dimension of from 0.5 to 100 µm.

The nonwoven layer suitably comprises preferably from 10 to 100% by weight, more preferably from 30 to 100% by weight, most preferably from 55 to 100% by weight of hydrophilic fibers, preferably inherently hydrophilic fibers. In addition to the hydrophilic fibers, the nonwoven layer may contain from 90 to 0% by weight of a high wet modulus, preferably inherently hydrophobic, fibers. The nonwoven layer may be formed from a single type of hydrophilic fiber or may contain hydrophilic fibers having different compositions, lengths and maximum cross-sectional dimensions.

In one preferred embodiment, the nonwoven layer is formed from air laid cellulosic fibers such as wood pulp fluff. Wood pulp fluff fibers are preferred for use due to their ready availability and due to the fact that the fibers are relatively inexpensive compared to synthetic polymeric fibers.

The nonwoven layer suitably has a basis weight of preferably from 10 to 200 gsm, more preferably from 20 to 150 gsm, most preferably from 25 to 125 gsm.

The nonwoven layer suitably has a density of preferably from 0.04 to 0.20 g/cm$^3$, more preferably from 0.06 to 0.16 g/cm$^3$, most preferably from 0.08 to 0.14 g/cm$^3$.

Typically the fluid-absorbent cores may contain a single type of superabsorbent particles or may contain superabsorbent particles derived from different kinds of superabsorbent material. Thus, it is possible to add superabsorbent particles from a single kind of polymer material or a mixture of superabsorbent particles from different kinds of polymer materials, e.g. a mixture of regular superabsorbent particles, derived from gel polymerization with superabsorbent particles, derived from dropletization polymerization. Alternatively it is possible to add superabsorbent particles derived from inverse suspension polymerization.

Alternatively it is possible to mix superabsorbent particles showing different feature profiles. Thus, the fluid-absorbent core may contain superabsorbent particles with uniform pH value, or it may contain superabsorbent particles with different pH values, e.g. two- or more component mixtures from superabsorbent particles with a pH in the range from 4.0 to 7.0. Preferably, applied mixtures deriving from mixtures of superabsorbent particles got from gel polymerization or inverse suspension polymerization with a pH in the range from 4.0 to 7.0 and superabsorbent particles got from dropletization polymerization.

The fluid-absorbent core comprises at least 75% by weight, preferably at least 80% by weight, more preferably at least 83% by weight, most preferably at least 85% by weight, of multicomponent superabsorbent particles.

The quantity of superabsorbent particles within the fluid-absorbent core is preferably from 3 to 20 g, more preferably from 6 to 14 g, most preferably from 8 to 12 g in the case of maxi-diapers, and in the case of incontinence products up to 50 g.

The types of adhesives are not particularly limited. A wide variety of thermoplastic compositions are suitable for use as pressure sensitive adhesives in the present invention.

Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefine or styrene block copolymer and mixture of waxes.

Suitable thermoplastic polymers are styrenic block copolymers including A-B-A triblock segments, A-B diblock segments and (A-B)n radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyalphaolefins and metallocene polyolefins.

The construction of the fluid-absorbent cores is made and controlled by the discrete application of adhesives as known to people skilled in the art. Examples would be e.g. Dispomelt 505B, Dispomelt Cool 1101, as well as other specific function adhesives manufactured by National Starch or Henkel.

Ultrathin fluid-absorbent cores are be formed by immobilization of superabsorbent particles on a substrate layer using adhesives. Preferably the superabsorbent particles form longitudinal strips or discrete spots. Other patterns of the superabsorbent particles are also possible.

Typically, the superabsorbent particles form a discontinuous layer on the substrate layer, i.e. a nonwoven layer, covered by a thermoplastic composition as adhesive forming discrete cavities, so that the superabsorbent particles are immobilized.

It is also possible to use a second substrate layer that comprises an adhesive instead of the thermoplastic composition.

In a preferred embodiment the ultrathin fluid-absorbent cores comprise at least two layers of immobilized superabsorbent particles.

Suitable fluid-absorbent cores may also include layers, which are formed by the process of manufacturing the fluid-absorbent article. The layered structure may be formed by subsequently generating the different layers in z-direction.

Alternatively a core-structure can be formed from two or more preformed layers to get a layered fluid-absorbent core. These uniform or different layers can be fixed to each other at their adjacent plane surfaces. Alternatively, the layers may be combined in a way that a plurality of chambers is formed, in which separately superabsorbent material is incorporated.

Further a composite structure can be formed from a carrier layer (e.g. a polymer film), onto which the superabsorbent material is affixed. The fixation can be done at one side or at both sides. The carrier layer may be pervious or impervious for body-fluids.

Typically fluid-absorbent articles comprising at least an upper liquid-pervious layer (A), at least a lower liquid-impervious layer (B) and at least one fluid-absorbent core between the layer (A) and the layer (B) besides other optional layers. The addition of a second fluid-absorbent core to the first fluid-absorbent core offers more possibilities in body fluid transfer and distribution. Moreover higher quantities of discharged body fluids can be retained. Having the opportunity of combining several layers showing a different superabsorbent particle concentration and content, it is possible to reduce the thickness of the fluid-absorbent article to a minimum even if there are several fluid-absorbent cores included.

Suitable fluid-absorbent articles are including single or multi-core systems in any combination with other layers which are typically found in fluid-absorbent articles. Preferred fluid-absorbent articles include single- or double-core systems; most preferably fluid-absorbent articles include a single fluid-absorbent core.

The fluid-absorbent core typically has a uniform size or profile. Suitable fluid-absorbent cores can also have profiled structures, concerning the shape of the core and/or the content of superabsorbent particles and/or the distribution of the superabsorbent particles and/or the dimensions of the different layers if a layered fluid-absorbent core is present.

These layers or foldings are preferably joined to each e.g. by addition of adhesives or by mechanical, thermal or ultrasonic bonding or combinations thereof. Superabsorbent particles may be comprised within or between the individual layers, e.g. by forming separate superabsorbent-layers.

The fluid-absorbent core may comprise additional additives typically present in fluid-absorbent articles known in the art. Exemplary additives are odor control additives and wetness indication additives.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disucci-nic acid.

Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids.

Suitable odor control additives are further perfumes such as allyl caproate, allyl cyclohexane-acetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevo-carveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Masking agents are also used as odor control additives. Masking agents are in solid wall material encapsulated perfumes. Preferably, the wall material comprises a fluid-soluble cellular matrix which is used for time-delay release of the perfume ingredient.

Further suitable odor control additives are transition metals such as Cu, Ag, and Zn, enzymes such as urease-inhibitors, starch, pH buffering material, chitin, green tea plant extracts, ion exchange resin, carbonate, bicarbonate, phosphate, sulfate or mixtures thereof.

Preferred odor control additives are green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from 0.5 to 300 gsm.

Newest developments propose the addition of wetness indication additives. Besides electrical monitoring the wetness in the fluid-absorbent article, wetness indication additives comprising a hot melt adhesive with a wetness indicator are known. The wetness indication additive changes the colour from yellow to a relatively dark and deep blue. This colour change is readily perceivable through the liquid-impervious outer material of the fluid-absorbent article. Existing wetness indication is also achieved via application of water soluble ink patterned on the backsheet which disappears when wet.

Suitable wetness indication additives comprising a mixture of sorbitan monooleate and polyethoxylated hydrogenated castor oil. Preferably, the amount of the wetness indication additive is in the range of 1 to 5% by weight related to the weight of the fluid-absorbent core.

The basis weight of the fluid-absorbent core is preferably in the range of 400 to 1200 gsm. The density of the fluid-absorbent core is preferably in the range of 0.1 to 0.50 g/cm$^3$. The thickness of the fluid-absorbent core is in the case of diapers preferably in the range of 1 to 5 mm, in the case of incontinence products preferably in the range of 3 to 15 mm.

Optional Acquisition-Distribution Layer (D)

An optional acquisition-distribution layer (D) is located between the upper layer (A) and the fluid-absorbent core (C) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

The acquisition-distribution layer comprises fibrous material and optionally superabsorbent particles.

The fibrous material may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof. Thus, suitable acquisition-distribution layers may contain cellulosic fibers, in particular wood pulp fluff. Examples of further suitable hydrophilic, hydrophobic fibers, as well as modified or unmodified natural fibers are given in the chapter "Liquid-pervious Layer (A)" above.

Especially for providing both fluid acquisition and distribution properties, the use of modified cellulosic fibers is preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of coatings and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by crosslink bonds in individualized form. Suitable chemical stiffening agents are typically monomeric crosslinking agents including $C_2$-$C_8$ dialdehyde, $C_2$-$C_8$ monoaldehyde having an acid functionality, and especially $C_2$-$C_9$ polycarboxylic acids.

Preferably the modified cellulosic fibers are chemically treated cellulosic fibers. Especially preferred are curly fibers which can be obtained by treating cellulosic fibers with citric acid. Preferably the basis weight of cellulosic fibers and modified cellulosic fibers is from 50 to 200 gsm.

Suitable acquisition-distribution layers further include synthetic fibers. Known examples of synthetic fibers are found in the Chapter "Liquid-pervious Layer (A)" above. 3D-polyethylene in the function of acquisition-distribution layer is preferred.

Further, as in the case of cellulosic fibers, hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Preferred acquisition-distribution layers comprise fibrous material and superabsorbent particles distributed within. The superabsorbent particles may be added during the process of forming the layer from loose fibers, or, alternatively, it is possible to add monomer solution after the formation of the layer and polymerize the coating solution by means of UV-induced polymerization technologies. Thus, "in situ"-polymerization is a further method for the application of superabsorbents.

Thus, suitable acquisition-distribution layers comprising from 80 to 100% by weight fibrous material and from 0 to 20% by weight multicomponent superabsorbent particles; preferably from 85 to 99.9% by weight fibrous material and from 0.1 to 15% by weight multicomponent superabsorbent particles; more preferably from 90 to 99.5% by weight fibrous material and from 0.5 to 10% by weight multicomponent superabsorbent particles; and most preferably from 95 to 99% by weight fibrous material and from 1 to 5% by weight multicomponent superabsorbent particles.

Preferred acquisition-distribution layers show basis weights in the range from 20 to 200 gsm, most preferred in the range from 40 to 50 gsm, depending on the concentration of superabsorbent particles.

Optional Tissue Layer (E)

An optional tissue layer is disposed immediately above and/or below (C).

The material of the tissue layer may comprise any known type of substrate, including webs, garments, textiles and films. The tissue layer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers.

Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands. Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearer's body, e.g. the waist and the legs to improve containment and fit. Leg elastics are placed between the outer and inner layers or the fluid-absorbent article, or between the outer cover and the bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system includes tape tabs, landing zone, elastomerics, pull ups and the belt system.

At least a part of the first waist region is attached to a part of the second waist region by the closing system to hold the fluid-absorbent article in place and to form leg openings and the waist of the fluid-absorbent article. Preferably the fluid-absorbent article is provided with a re-closable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations thereof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a nonwoven spunbond web attacked to the backing material.

Thus suitable landing zones can be made by spunbonding. Spunbonded nonwovens are made from melt-spun fibers formed by extruding molten thermoplastic material. Preferred is bioriented polypropylene (BOPP), or brushed/closed loop in the case of mechanical closing systems.

Further, suitable mechanical closing systems including elastic units serving as a flexible waist band for fluid-absorbents articles, such as pants or pull-ups. The elastic units enabling the fluid-absorbent article to be pulled down by the wearer as e.g. a training pant.

Suitable pants-shaped fluid-absorbent article has front section, rear section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat. Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single- or double fluid-absorbent core-system.

Suitable fluid-storage layers of the fluid-absorbent core comprising homogenous or inhomogeneous mixtures of fibrous materials comprising superabsorbent particles homogeneously or inhomogeneously dispersed in it. Suitable fluid-storage layers of the fluid-absorbent core including a layered fluid-absorbent core-system comprising homogenous mixtures of fibrous materials and optionally comprising superabsorbent particles, whereby each of the layers may be prepared from any fibrous material by means known in the art.

In order to immobilize the superabsorbent particles, the adjacent layers are fixed by the means of thermoplastic materials, thereby building connections throughout the whole surface or alternatively in discrete areas of junction. For the latter case, cavities or pockets are built carrying the superabsorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between 0.5 mm and 2 mm. Fluid-absorbent articles comprising areas of junction show a better wet strength.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

The superabsorbent particles and the fluid-absorbent articles are tested by means of the test methods described below.

Methods:

Dry SAP Shake Out (drySAPLoss)

The dry SAP shake-out of superabsorbent particles is determined using a rectangle core sample having a size of 7 inch×4 inch (17.8 cm×10.2 cm) that is cut from the center of a fluid-absorbent core. The weight of the cut core sample is recorded as Before Shake Dry Weight ($W_{b-dry}$). The dry core sample is carefully placed on top of an 850 micron U.S.A. standard testing sieve (VWR International LLC; Arlington Heights; U.S.A.). The sieve with the dry core sample is installed on a Retsch® AS 200 sieve shaker (Retsch GmbH; Haan; Gemany) and shaken at a pre-set amplitude of 2.00 for 5 minutes. Next, the dry core sample is picked up on the short end and vertically transferred to a weighting pan. The wet core sample is recorded as After Shake Dry Weight ($W_{a-dry}$). The dry SAP shake-out (drySAPLoss) is calculated as follows:

$$drySAPLoss[\text{wt. \%}] = \frac{W_{b-dry} - W_{a-dry}}{W_{b-dry}}$$

Wet SAP Shake Out (wetSAPLoss)

The wet SAP shake-out of superabsorbent particles is determined using a rectangle core sample having a size of 7 inch×4 inch (17.8 cm×10.2 cm) that is cut from the center of a fluid-absorbent core. The weight of the cut core sample is recorded as Dry Weight ($W_{dry}$). The dry core sample is laid in a pan and 10 g of 0.9% NaCl solution per gram of Dry Weight are added to the core sample homogeneously. Five minutes after all free liquid has been absorbed by the core sample, the wet core sample is weighted and recorded as Before Shake Wet Weight ($W_{b-wet}$). The wet core sample is carefully placed on top of an 850 micron U.S.A. standard testing sieve (VWR International LLC; Arlington Heights; U.S.A.). The sieve with the wet core sample is installed on a Retsch® AS 200 sieve shaker (Retsch GmbH; Haan; Gemany) and shaken at a pre-set amplitude of 2.00 for 5 minutes. Next, the wet core sample is picked up on the short end and vertically transferred to a weighting pan. The wet core sample is recorded as After Shake Wet Weight ($W_{a-wet}$). The wet SAP shake-out (wetSAPLoss) is calculated as follows:

$$wetSAPLoss[\text{wt. \%}] = \frac{W_{b\text{-}wet} - W_{a\text{-}wet}}{W_{b\text{-}wet}}$$

EXAMPLES

Preparation of the Multicomponent Superabsorbent Particles

Example 1

A monomer mixture containing acrylic acid (270 grams), deionized water (810 grams), methylene-bisacrylamide (0.4 grams), sodium persulfate (0.547 grams), and 2-hydroxy-2-methyl-1-phenyl-propan-1-one (0.157 grams) was prepared, then sparged with nitrogen for 15 minutes. The monomer mixture was placed into a shallow glass dish, then the monomer mixture was polymerized under 15 mW/cm$^2$ of UV light for 25 minutes. The resulting polyacrylic acid was a rubbery gel.

The rubbery polyacrylic acid gel was cut into small pieces, then extruded through a KitchenAid Model K5SS mixer with meat grinder attachment. The extruded gel was dried in a forced-air oven at 120° C., and finally ground and sized through sieves to obtain the desired particle size. This procedure provided a lightly crosslinked polyacrylic acid hydrogel with a degree of neutralization of zero (DN=0).

Example 2

To 2 liters of a 3% by weight aqueous polyvinyl amine solution was added 0.18 g of ethyleneglycol diglycidyl ether (EGDGE). The resulting mixture was stirred to dissolve the EGDGE, then the mixture was heated to 60° C. and held for one hour to gel. The gel was heated to 80° C. and held until 90% of the water was removed. The resulting gel then was extruded and dried to a constant weight at 80° C. The dried, lightly crosslinked polyvinylamine then was cryogenically milled to form a granular material.

This procedure provided a lightly crosslinked polyvinyl amine hydrogel with a degree of neutralization of zero (DN=0).

Example 3

Thirty grams of the polyvinyl amine hydrogel of Example 2 were extruded through a KitchenAid Model K5SS mixer with meat grinder attachment. Thirty grams of the polyacrylic acid hydrogel of Example 1 also were extruded through a KitchenAid Model K5SS mixer with meat grinder attachment. The two extrudates then were combined via hand mixing, followed by extruding the resulting mixture two times using the meat grinder. The extruded product then was dried for 16 hours at 60° C., milled and sized to 180-710 µm. The procedure yields multicomponent SAP particles containing microdomains of poly polyvinylamine and polyacrylic acid, and having polyvinylamine/polyacrylic acid weight ratio of 50/50.

Preparation of the Fluid-Absorbent Cores

Example 4

A first substrate layer was laid on a flat cardboard and covered with a pattern template. The first substrate was a commercially available 15 gsm nonwoven (AVGOL American Inc.; Mocksville; U.S.A.) having a size of 14.5 inch×4.5 inch (36.8 cm×11.4 cm).

The template was a commercially available stainless steel plate having square end slots and an open area of 40% (Direct Metals Company, LLC; Kennesaw; U.S.A.). The template had a size of 10 inch×14 inch (25.4 cm×35.6 cm). The slots had a size of ¼ inch×⅜ inch (0.64 cm×0.95 cm) and were side staggered having end and side bars of 3/16 inch (0.48 cm).

11 g of multicomponent SAP particles prepared in example 3 were added as evenly as possible onto the template and then evenly distributed with a smooth rubber blade to create a pattern of the multicomponent SAP particles on the first substrate layer.

A piece of a commercially available pressure sensitive adhesive having 20 gsm (BASF Corporation; Monaca; U.S.A.) on a release paper was transferred onto a second substrate layer (corresponding to 0.84 g adhesive). Next, the template on the first substrate layer was carefully removed and the second substrate layer was placed on the top of the first substrate layer with the adhesive side of the second substrate layer facing the top side with the multicomponent SAP particles of the first substrate layer. The second substrate was a commercially available 15 gsm nonwoven (AVGOL American Inc.; Mocksville; U.S.A.) having a size of 14.5 inch×4.5 inch (36.8 cm×11.4 cm).

The single layered fluid-absorbent core was transferred with the cardboard into a Carver® Press model Auto Series 4425.4DI0A01 (Carver Inc.; Wabash; U.S.A.). At ambient temperature (20 to 22° C.), the press was pre-set to 10,000 lbs (corresponding to 1,054 kPa) and immediately stopped once the pre-set pressure was reached.

The resulting fluid-absorbent core was analyzed, the results are summerized in table 1.

Example 5

Example 4 was repeated, except that the pattern template was a commercially available perforated plastic piece having round holes (United States Plastic Corporation; Lima Ohio; U.S.A.). The template had a size of 4.5 inch×14 inch (11.4 cm×35.6 cm) and a thickness of ⅛ inch (0.3 cm). The holes had a diameter of ¼ inch (0.64 cm) and were side staggered (every other hole was taped off) having end and side bars of ½ inch (1.3 cm). The resulting fluid-absorbent core was analyzed, the results are summerized in table 1.

Example 6

Example 4 was repeated, except that the first and the second substrate were a 17 gsm forming tissue (Cellu Tissue Holdings, Inc.; East Hartford; U.S.A.) having a size of 14.5 inch×4.5 inch (36.8 cm×11.4 cm). The resulting fluid-absorbent core was analyzed, the results are summerized in table 1.

Example 7

Example 4 was repeated, except that the first and the second substrate were a 17 gsm forming tissue (Cellu Tissue Holdings, Inc.; East Hartford; U.S.A.) having a size of 14.5 inch×4.5 inch (36.8 cm×11.4 cm) and that the pattern template was a commercially available perforated plastic piece having round holes (United States Plastic Corporation; Lima Ohio; U.S.A.). The template had a size of 4.5 inch×14 inch (11.4 cm×35.6 cm) and a thickness of ⅛ inch (0.3 cm). The holes had a diameter of ¼ inch (0.64 cm) and were side staggered (every other hole was taped off) having end and side bars of ½ inch (1.3 cm). The resulting fluid-absorbent core was analyzed, the results are summerized in table 1.

Example 8

Example 7 was repeated, except that the fluid-absorbent core was laminated by pressing at 15,000 lbs (corresponding to 1,581 kPa) for 5 minutes using a Carver® Press model Auto Series 4425.4DI0A01 (Carver Inc.; Wabash; U.S.A.). The press plates are heated to 60° C. The resulting fluid-absorbent core was analyzed, the results are summerized in table 1.

TABLE 1

Results of the SAP shake-out procedure
(fluid-absorbent cores with adhesive)

| Fluid-absorbent core | superabsorbent particles | substrate | pattern template | drySAPLoss | wetSAPLoss |
|---|---|---|---|---|---|
| Example 4 | Example 3 | nonwoven | square slots | 0.13 wt. % | 1.6 wt. % |
|  | ASAP ® 531T | nonwoven | square slots | 1.29 wt. % | 50.1 wt. % |
|  | Hysorb ® B7055 | nonwoven | square slots | 1.9 wt. % | 47.2 wt. % |
|  | Hysorb ® T8760 | nonwoven | square slots | 2.21 wt. % | 16.8 wt. % |
| Example 5 | Example 3 | nonwoven | round holes | 1.11 wt. % | 3.6 wt. % |
|  | ASAP ® 531T | nonwoven | round holes | 2.42 wt. % | 29.5 wt. % |
|  | Hysorb ® B7055 | nonwoven | round holes | 1.82 wt. % | 21.0 wt. % |
|  | Hysorb ® T8760 | nonwoven | round holes | 5.4 wt. % | 13.6 wt. % |
| Example 6 | Example 3 | tissue paper | square slots | 0.00 wt. % | 0.3 wt. % |
|  | ASAP ® 531T | tissue paper | square slots | 0.84 wt. % | 65.2 wt. % |
|  | Hysorb ® B7055 | tissue paper | square slots | 1.45 wt. % | 42.1 wt. % |
|  | Hysorb ® T8760 | tissue paper | square slots | 0.77 wt. % | 17.5 wt. % |
| Example 7 | Example 3 | tissue paper | round holes | 1.24 wt. % | 4.5 wt. % |
| Example 8*) | Example 3 | tissue paper | round holes | 0.00 wt. % | 4.0 wt. % |
|  | ASAP ® 531T | tissue paper | round holes | 2.51 wt. % | 28.7 wt. % |
|  | Hysorb ® B7055 | tissue paper | round holes | 2.05 wt. % | 12.5 wt. % |
|  | Hysorb ® T8760 | tissue paper | round holes | 2.51 wt. % | 21.6 wt. % |

*)60° C. compression
ASAP ® 531T, Hysorb ® B7055, and Hysorb ® T8760 are commercially availabe superabsorbent particles (BASF SE; Ludwigshafen; Germany).

Example 9 (Comparative)

A first substrate layer was laid on a flat cardboard and covered with a pattern template. The first substrate was a commercially available 15 gsm nonwoven (AVGOL American Inc.; Mocksville; U.S.A.) having a size of 14.5 inch×4.5 inch (36.8 cm×11.4 cm).

The template was a commercially available perforated plastic piece having round holes (United States Plastic Corporation; Lima Ohio; U.S.A.). The template had a size of 4.5 inch×14 inch (11.4 cm×35.6 cm) and a thickness of ⅛ inch (0.3 cm). The holes had a diameter of ¼ inch (0.64 cm) and were side staggered (every other hole was taped off) having end and side bars of ½ inch (1.3 cm).

8 g of multicomponent SAP particles prepared in example 3 were added as evenly as possible onto the template and then evenly distributed with a smooth rubber blade to create a pattern of the multicomponent SAP particles on the first substrate layer.

Next, the template on the first substrate layer was carefully removed and the second substrate layer was placed on the top of the first substrate layer facing the top side with the multicomponent SAP particles of the first substrate layer and no adhesive was added to the substrate. The second substrate was a commercially available 15 gsm nonwoven (AVGOL American Inc.; Mocksville; U.S.A.) having a size of 14.5 inch×4.5 inch (36.8 cm×11.4 cm).

The single layered fluid-absorbent core was transferred with the cardboard into a Carver® Press model Auto Series 4425.4DI0A01 (Carver Inc.; Wabash; U.S.A.). The fluid-absorbent core was laminated by pressing at 15,000 lbs (corresponding to 1,581 kPa) for 5 minutes using a Carver® Press model Auto Series 4425.4DI0A01 (Carver Inc.; Wabash; U.S.A.). The press plates are heated to 60° C.

The resulting fluid-absorbent core was analyzed, the results are summerized in table 2.

Example 10 (Comparative)

Example 9 was repeated, except that the first and the second substrate were a 17 gsm forming tissue (Cellu Tissue Holdings, Inc.; East Hartford; U.S.A.) having a size of 14.5 inch×4.5 inch (36.8 cm×11.4 cm). The resulting fluid-absorbent core was analyzed, the results are summerized in table 2.

Example 11 (Comparative)

Example 9 was repeated, except that the first and the second substrate were a 17 gsm forming tissue (Cellu Tissue Holdings, Inc.; East Hartford; U.S.A.) having a size of 14.5 inch×4.5 inch (36.8 cm×11.4 cm) and that the pattern template was a commercially available stainless steel plate having square end slots and an open area of 40% (Direct Metals Company, LLC; Kennesaw; U.S.A.). The template had a size of 10 inch×14 inch (25.4 cm×35.6 cm). The slots had a size of ¼ inch×⅜ inch (0.64 cm×0.95 cm) and were side staggered having end and side bars of 3/16 inch (0.48 cm). The resulting fluid-absorbent core was analyzed, the results are summerized in table 2.

Example 12 (Comparative)

Example 9 was repeated, except that the first and the second substrate were a 17 gsm forming tissue (Cellu Tissue Holdings, Inc.; East Hartford; U.S.A.) having a size of 14.5 inch×4.5 inch (36.8 cm×11.4 cm) and a template having a 9.45 inch×4.72 inch (24.0 cm×13.5 cm) rectangular cutout was used instead of a pattern template. The resulting fluid-absorbent core was analyzed, the results are summerized in table 2.

Example 13 (Comparative)

A first substrate layer was laid on a flat cardboard and covered with a template having a 9.45 inch×4.72 inch (24.0 cm×13.5 cm) rectangular cutout. The first substrate was a 17 gsm forming tissue (Cellu Tissue Holdings, Inc.; East Hartford; U.S.A.) having a size of 14.5 inch×4.5 inch (36.8 cm×11.4 cm).

8 g of multicomponent SAP particles prepared in example 3 were added as evenly as possible onto the template and then evenly distributed with a smooth rubber blade on the first substrate layer.

Next, the template on the first substrate layer was carefully removed and the second substrate layer was placed on the top of the first substrate layer facing the top side with the multicomponent SAP particles of the first substrate layer. The second substrate was a 17 gsm forming tissue (Cellu Tissue Holdings, Inc.; East Hartford; U.S.A.) having a size of 14.5 inch×4.5 inch (36.8 cm×11.4 cm).

The second substrate layer was covered with the pattern template and further 8 g of multicomponent SAP particles prepared in example 3 were added as evenly as possible onto the template and then evenly distributed with a smooth rubber blade to create a homogeneous layer of multicomponent SAP particles on the second substrate layer.

Next, the template on the second substrate layer was carefully removed and the third substrate layer was placed on the top of the second substrate layer facing the top side with the multicomponent SAP particles of the second substrate layer. The third substrate was a commercially available 15 gsm nonwoven (AVGOL American Inc.; Mocksville; U.S.A.) having a size of 14.5 inch×4.5 inch (36.8 cm×11.4 cm).

The multi layered fluid-absorbent core was transferred with the cardboard into a Carver® Press model Auto Series 4425.4DI0A01 (Carver Inc.; Wabash; U.S.A.). The fluid-absorbent core was laminated by pressing at 15,000 lbs (corresponding to 1,581 kPa) for 5 minutes using a Carver® Press model Auto Series 4425.4DI0A01 (Carver Inc.; Wabash; U.S.A.). The press plates are heated to 60° C.

The resulting fluid-absorbent core was analyzed, the results are summerized in table 2.

TABLE 2

Results of the SAP shake-out procedure
(fluid-absorbent cores without adhesive)

| Fluid-absorbent core | superabsorbent particles | substrate | pattern template | drySAPLoss | wetSAPLoss |
|---|---|---|---|---|---|
| Example 9 | Example 3 | nonwoven | round holes | 15.1 wt. % | 96.9 wt. % |
| Example 10 | Example 3 | tissue paper | round holes | 2.28 wt. % | 92.2 wt. % |
| Example 11 | Example 3 | tissue paper | square slots | 0.00 wt. % | 79.9 wt. % |
| Example 12 | Example 3 | tissue paper | without | 0.42 wt. % | 48.8 wt. % |
| Example 13*) | Example 3 | tissue paper | without | 0.36 wt. % | 82.0 wt. % |

*)multi layered fluid-absorbent core
ASAP ® 531T, Hysorb ® B7055, and Hysorb ® T8760 are commercially availabe superabsorbent particles (BASF SE; Ludwigshafen; Germany) prepared by customary solution polymerization.

What is claimed:

1. A fluid-absorbent core comprising a substrate layer, at least 75% by weight of multicomponent superabsorbent particles comprising at least one crosslinked basic water-absorbing resin having a degree of neutralization of 0 to 50% and at least one crosslinked acidic water-absorbing resin having a degree of neutralization of 0 to 50%, less than 10% by weight of fibers, and an adhesive, wherein a wet SAP shake-out of superabsorbent particles out of the fluid-absorbent core is less than 10% by weight.

2. The fluid-absorbent core according to claim 1, wherein the fluid-absorbent core is essentially free of cellulose pulp fluff.

3. The fluid-absorbent core according to claim 1, wherein the crosslinked basic water-absorbing resin and the crosslinked acidic water-absorbing resin are present in a weight ratio of 5:95 to 95:5.

4. The fluid-absorbent core according to claim 1, wherein the crosslinked basic water-absorbing resin is a poly(vinylamine).

5. The fluid-absorbent core according to claim 1, wherein the crosslinked acidic water-absorbing resin is a polyacrylic acid.

6. The fluid-absorbent core according to claim 1, wherein the fluid-absorbent core comprises not more than 10% by weight of the adhesive.

7. The fluid-absorbent core according to claim 1, wherein a dry SAP shake-out of superabsorbent particles out of the fluid-absorbent core is less than 5% by weight.

8. The fluid-absorbent core according to claim 1, wherein the fluid-absorbent core comprises at least 85% by weight of multicomponent superabsorbent particles.

9. The fluid-absorbent core according to claim 1, wherein the wet SAP shake-out of superabsorbent particles out of the fluid-absorbent core is less than 5% by weight.

10. The fluid-absorbent core according to claim 9, wherein a dry SAP shake-out of superabsorbent particles out of the fluid-absorbent core is less than 2% by weight.

11. The fluid-absorbent core according to claim 1, wherein a dry SAP shake-out of superabsorbent particles out of the fluid-absorbent core is less than 2% by weight.

12. The fluid-absorbent core according to claim 1, wherein the adhesive is a pressure sensitive adhesive.

13. The fluid-absorbent core according to claim 1, wherein the substrate layer is a nonwoven layer.

14. The fluid-absorbent core according to claim 1, wherein the fluid-absorbent core comprises at least two layers of the multicomponent superabsorbent particles.

15. The fluid-absorbent core according to claim 1, wherein the multicomponent superabsorbent particles are placed in discrete regions.

16. The fluid-absorbent article, comprising
   a) an upper liquid-pervious layer,
   b) a lower liquid-impervious layer and
   c) a fluid-absorbent core according to claim 1 between the layer (A) and the layer (B),
   d) an optional acquisition-distribution layer between (A) and (C),
   e) an optional tissue layer disposed immediately above and/or below (C); and
   f) and other optional components.

* * * * *